(12) United States Patent
Musa et al.

(10) Patent No.: US 11,753,484 B2
(45) Date of Patent: *Sep. 12, 2023

(54) CELLULOSE ETHER-LACTAM HYBRID POLYMERS, COMPOSITIONS, AND METHODS FOR PREPARING AND USING THE HYBRID POLYMERS

(71) Applicant: HERCULES LLC, Wilmington, DE (US)

(72) Inventors: Osama M. Musa, Bedminster, NJ (US); Daiqiang Xu, Newark, DE (US); Todd Andrew Brugel, Wilmington, DE (US)

(73) Assignee: HERCULES LLC, Wilmington, DE (US)

( * ) Notice: Subject to any disclaimer, the term of this patent is extended or adjusted under 35 U.S.C. 154(b) by 379 days.

This patent is subject to a terminal disclaimer.

(21) Appl. No.: 16/760,870

(22) PCT Filed: Nov. 5, 2018

(86) PCT No.: PCT/US2018/059165
§ 371 (c)(1),
(2) Date: Apr. 30, 2020

(87) PCT Pub. No.: WO2019/090207
PCT Pub. Date: May 9, 2019

(65) Prior Publication Data
US 2021/0171664 A1 Jun. 10, 2021

Related U.S. Application Data

(60) Provisional application No. 62/581,104, filed on Nov. 3, 2017.

(51) Int. Cl.
| | | |
|---|---|---|
| *C08B 11/00* | (2006.01) | |
| *C08L 1/28* | (2006.01) | |
| *C08B 15/00* | (2006.01) | |
| *C08G 69/24* | (2006.01) | |
| *C08G 69/48* | (2006.01) | |
| *A61K 9/16* | (2006.01) | |
| *A61K 31/536* | (2006.01) | |

(52) U.S. Cl.
CPC ............ *C08B 15/005* (2013.01); *C08B 11/00* (2013.01); *C08G 69/24* (2013.01); *C08G 69/48* (2013.01); *C08L 1/288* (2013.01); *A61K 9/16* (2013.01); *A61K 31/536* (2013.01)

(58) Field of Classification Search
None
See application file for complete search history.

(56) References Cited

U.S. PATENT DOCUMENTS 3,494,826 A 2/1970 Scheiber
4,831,097 A * 5/1989 Chuang .................. A61Q 19/10
424/70.13

(Continued)

FOREIGN PATENT DOCUMENTS

WO WO 2009/110001 A1 9/2009

OTHER PUBLICATIONS

References cited in the International Search Report of International Application No. PCT/US18/59165, dated Feb. 27, 2019.

*Primary Examiner* — Eric Olson
(74) *Attorney, Agent, or Firm* — William J. Davis; Nathalie Tietcheu

(57) ABSTRACT

The present invention provides novel hybrid polymers having unique physical properties. The hybrid polymers comprise a cellulose ether moiety, a linking group moiety, a spacer group moiety, and a lactam moiety. The present invention also provides compositions comprising the hybrid polymers and methods for preparing and using the hybrid polymers.

In a first embodiment, the hybrid polymers have the structure:

$$A\text{-}(L_1\text{-}S\text{—}(B)_k)_q$$

wherein A is derived from a cellulose ether moiety comprising a —OH group; $L_1$ is a linking group moiety selected from the group consisting of urethanes, amides, esters, carbonates, and phosphate esters, or is derived from a moiety selected from the group consisting of anhydrides, cyclic ethers, and aziridines; S is a spacer group moiety, selected from the group consisting of straight- or branched-chain functionalized and unfunctionalized alkyl, cycloalkyl, alkenyl, and aryl groups, wherein any of the above groups may be with or without heteroatoms, or is a direct bond; and B is a lactam moiety; wherein $k \geq 1$ and $q \geq 1$.

In a second embodiment, the hybrid polymers have the structure:

$$A\text{-}(L_2\text{-}S\text{—}B)_y$$

wherein A is derived from a cellulose ether moiety comprising a —OH group; $L_2$ is an ether linking group moiety; S is a spacer group moiety, selected from the group consisting of straight- or branched-chain functionalized and unfunctionalized alkyl, cycloalkyl, alkenyl, and aryl groups, wherein any of the above groups may be with or without heteroatoms, or is a direct bond; and B is a lactam moiety; wherein $y \geq 1$; with the proviso that when the cellulose ether moiety is hydroxyethyl cellulose, $\text{-}(L_2\text{-}S\text{—}B)_y$ is not derived from 1-(hydroxymethyl)-2-pyrrolidinone.

17 Claims, No Drawings

(56) References Cited

U.S. PATENT DOCUMENTS

| | | | | |
|---|---|---|---|---|
| 5,037,930 A | * | 8/1991 | Shih | A61K 8/731 |
| | | | | 527/315 |
| 10,081,757 B2 | * | 9/2018 | Lei | C08B 15/00 |
| 2012/0134942 A1 | | 5/2012 | Thomai Des | |

* cited by examiner

CELLULOSE ETHER-LACTAM HYBRID POLYMERS, COMPOSITIONS, AND METHODS FOR PREPARING AND USING THE HYBRID POLYMERS

FIELD OF THE INVENTION

The present invention provides novel hybrid polymers having unique physical properties. The hybrid polymers comprise a cellulose ether moiety, a linking group moiety, a spacer group moiety, and a lactam moiety. The present invention also provides compositions comprising the hybrid polymers and methods for preparing and using the hybrid polymers.

BACKGROUND OF THE INVENTION

Cellulose ether and lactam polymers possess very desirable functional properties, which make them useful as additives for many applications including pharmaceutical excipients, coatings, shampoos, conditioners, and cement additives. Cellulose ethers, such as methylcellulose, carboxymethyl cellulose, hydroxyethyl cellulose, and hydroxypropyl methylcellulose, are useful as rheology modifiers, tablet binders, tablet controlled release agents, film fonners, and conditioners. Lactam polymers, such as α-lactam (α-aziridinone), β-lactam (β-propiolactam), γ-lactam (γ-butyrolactam), δ-lactam (δ-valerolactam), and ε-lactam (ε-caprolactam), are useful as dispersives, adhesives, tablet binders, wetting agents, and film-forming agents.

Conventional cellulose polymers used to solubilize poorly water-soluble drugs in hot-melt applications tend to lack anti-nucleation properties needed to prevent recrystallization. Conventional cellulose polymers having anti-nucleating agents and drug solubilizers tend to have high Tg (glass transition) for hot melt extrusions.

Modified cellulose ethers are disclosed in U.S. Pat. Nos. 6,867,262, 7,357,987, and 6,077,319. Modified cellulose ethers are also disclosed in United States patent publication application no. US/2007/0090577A1, WO/2011/017223, and *Journal of PolVmer Science, PartA: Polymer Chemistry* 2015, 53, 68-78.

Accordingly, it would be desirable to combine cellulose ether moieties and lactam moieties in a hybrid polymer to provide a hybrid polymer having very desirable physical properties with the properties of both polymeric moieties. The combination would provide enhanced application performance in many fields such as pharmaceuticals, foods, beverages, coatings, paints, energy sector agents, oral care, skin care, hair care, cosmetics, toiletry, household and cleaning products, industrial and institutional cleaning products, disinfecting products, opthalmics, injectables, sanitary products, agricultural products, textiles, biocides, preservatives, and laundry products.

SUMMARY OF THE INVENTION

In a first embodiment, the hybrid polymers have the structure:

$$A\text{-}(L_1\text{-}X\text{—}(B)_k)_q$$

wherein A is derived from a cellulose ether moiety comprising a —OH group;
$L_1$ is a linking group moiety selected from the group consisting of urethanes, amides, esters, carbonates, and phosphate esters, or is derived from a moiety selected from the group consisting of anhydrides, cyclic ethers, and aziridines;
S is a spacer group moiety, selected from the group consisting of straight- or branched-chain functionalized and unfunctionalized alkyl, cycloalkyl, alkenyl, and aryl groups, wherein any of the above groups may be with or without heteroatoms, or is a direct bond; and
B is a lactam moiety;
wherein k≥1 and q≥1.

In a second embodiment, the hybrid polymers have the structure:

$$A\text{-}(L_2\text{-}X\text{—}B)_y$$

wherein A is derived from a cellulose ether moiety comprising a —OH group;
$L_2$ is an ether linking group moiety;
X is a spacer group moiety, selected from the group consisting of straight- or branched-chain functionalized and unfunctionalized alkyl, cycloalkyl, alkenyl, and aryl groups, wherein any of the above groups may be with or without heteroatoms, or is a direct bond; and
B is a lactam moiety;
wherein y≥1;
with the proviso that when the cellulose ether moiety is hydroxyethyl cellulose, -($L_2$-X—B)$_y$, is not derived from 1-(hydroxymethyl)-2-pyrrolidinone.

The present invention also provides compositions having enhanced application performance in various fields of end-user applications including, but not limited to, pharmaceuticals, foods and beverages, coatings, paints, energy sector agents, performance materials, oral care, skin care, hair care, cosmetics, toiletry, household and cleaning products, industrial and institutional cleaning products, disinfecting products, opthalmics, injectables, sanitary products, agricultural products, textiles, biocides, preservatives, consumer products, and laundry products. The hybrid polymers, having very desirable properties, combine the properties of both cellulose ether moieties and lactam moieties, thus providing enhanced application performance in various fields.

DETAILED DESCRIPTION OF THE INVENTION

The present invention provides novel hybrid polymers having unique physical properties. The hybrid polymers comprise a cellulose ether moiety, a linking group moiety, a spacer group moiety, and a lactam moiety. The hybrid polymers of the present invention combine the properties of cellulose ether moieties and lactam moieties into polymers having very desirable properties. The present invention also provides compositions comprising the hybrid polymers and methods for preparing and using the hybrid polymers.

All percentages, parts, proportions, and ratios as used herein are by weight of the total composition, unless otherwise specified. All such weights as they pertain to listed ingredients are based on the active level and therefore do not include solvents or by-products that may be included in commercially available materials, unless otherwise specified.

All references to singular characteristics or limitations of the present invention shall include the corresponding plural characteristics or limitations, and vice-versa, unless otherwise specified or clearly implied to the contrary by the context in which the reference is made.

Numerical ranges as used herein are intended to include every number and subset of numbers contained within that range, whether specifically disclosed or not. Further, these numerical ranges should be construed as providing support for a claim directed to any number or subset of numbers in that range.

All publications, articles, papers, patents, patent publications, and other references cited herein are hereby incorporated herein in their entireties for all purposes to the extent consistent with the disclosure herein.

As used herein, the following terms, unless otherwise stated, have the meanings set out below.

The term "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or."

The term "about" refers to a difference of 10% from the value specified. Numerical ranges as used herein are meant to include every number and subset of numbers enclosed within that range, whether particularly disclosed or not. All percentages, parts, proportions, and ratios, as used herein, are by weight of the total composition, unless otherwise specified.

The term "alkyl" refers to a functionalized or unfunctionalized monovalent straight-chain, branched-chain or cyclic $C_1$-$C_{60}$ group optionally having one or more heteroatoms. Particularly, an alkyl is a $C_1$-$C_{45}$ group and more particularly, a $C_1$-$C_{30}$ group. Particular, yet non-limiting, examples of alkyl groups include methyl, ethyl, n-propyl, isopropyl, n-butyl, isobutyl, tert-butyl, cyclobutyl, n-pentyl, isopentyl, cyclopentyl, n-hexyl, cyclohexyl, n-heptyl, cyclyheptyl, methylcyclohexyl, n-octyl, 2-ethylhexyl, tert-octyl, iso-norbornyl, n-dodecyl, tert-dodecyl, n-tetradecyl, n-hexadecyl, n-octadecyl, and n-eicosyl.

The term "alkyl (alk) acrylate" refers to an alkyl ester of an acrylic acid or an alkyl acrylic acid.

The term "alkyl (alk) acrylamide" refers to an alkyl amide of an acrylic acid or an alkyl acrylic acid.

The term "alkylene" refers to a functionalized or unfunctionalized divalent straight-chain, branched-chain or cyclic $C_1$-$C_{40}$ group optionally having one or more heteroatoms. Particularly, an alkylene is a $C_1$-$C_{45}$ group and more particularly, a $C_1$-$C_{30}$ group. Particular, yet non-limiting, examples of alkylene groups include —$CH_2$—, —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, —$CH_2$—$CH_2$—$CH_2$—$CH_2$—$CH_2$—$CH_2$—$CH_2$—, cyclopropylene, cyclobutylene, cyclopentylene, cyclohexylene, and the like.

The term "anhydride" or "acid anhydride" refers to an organic atom that has two acyl groups bonded to the same oxygen atom.

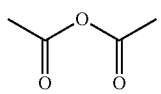

The term "are each independently selected from the group consisting of . . . " means that when a group appears more than once in a structure, that group may be independently selected each time it appears. For example, in the structure below:

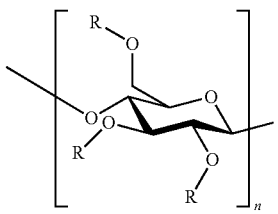

A

R appears more than once. The term "are each independently selected from the group consisting of" means that each R group may be the same or different.

The term "aryl" refers to a functional group derived from an aromatic hydrocarbon. The aromatic hydrocarbon can be mononuclear or polynuclear. Examples of aryl group of the mononuclear type include phenyl, tolyl, xylyl, mesityl, cumlenyl, and the like. Examples of aryl group of the polynuclear type include naphthyl, anthryl, phenanthryl, and the like. The aryl group can have at least one substituent selected from halogen, hydroxy, cyano, carboxy, carbamoyl, nitro, amino, aminomethyl, lower alkyl, lower alkoxy, mercapto, trichloroethyl, or trifluoromethyl. Examples of such substituted aryl groups include 2-fluorophenyl, 3-nitrophenyl, 4-nitrophenyl, 4-methoxyphenyl, 4-hydroxyphenyl, and the like.

The term "aziridine" refers to a three-membered heterocycle organic compound with one amine group (—NH—) and two methylene bridges (—$CH_2$—)

The term "branched and unbranched alkyl groups" refers to alkyl groups, which may be straight chained or branched. Particularly, the term refers to alkyl groups having from 1 to about 60 carbon atoms, more particularly, from 1 to about 30 carbon atoms, and yet more particularly from 1 to about 6 carbon atoms. Branched groups include isopropyl, tert-butyl, and the like.

The term "cellulose ether moiety comprising a —OH group" refers to a moiety having the structure:

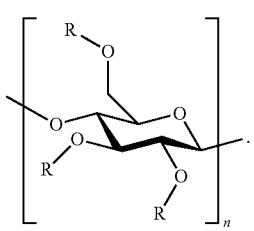

The moiety may also have the structure:

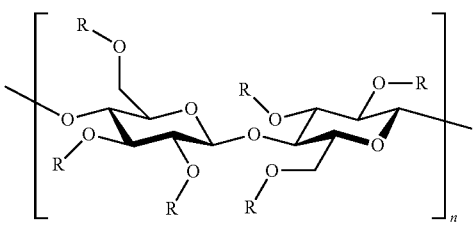

wherein n is an integer ranging from 1 to about 2000 or more.

The term "comprising" refers to optional compatible components that can be used provided that the important ingredients are present in the suitable form and concentrations. The term "comprising" thus encompasses and includes the more restrictive terms "consisting of" and "consisting essentially of" which can be used to characterize the essential ingredients such as cellulose ethers moieties, lactam moieties, linking groups and/or hybrid polymers.

The term "cycloalkyl group" refers to a non-aromatic mono- or multicyclo ring system having from about 3 to about 10 carbon atoms. The cycloalkyl group can be partially unsaturated. The cycloalkyl group can also be substituted with an alkyl group substituent as defined herein. The cycloalkyl chain may contain an oxygen, sulfur, or substituted or unsubstituted nitrogen atom, wherein the nitrogen substituent may be hydrogen, alkyl, substituted alkyl, aryl, or substituted aryl, thus providing a heterocyclo group. Representative monocyclo cycloalkyl rings include, but are not limited to, cyclopropyl, cyclobutyl, cyclopentyl, cyclohexyl, cycloheptyl, and the like. Further, the cycloalkyl group can be substituted with a linking group, such as an alkyl group, alkylene group, and the like, to form cyclopropylmethyl group, cyclobutylmethyl group, and the like. The cycloalkyl group may also be a multicyclo cycloalkyl rings such as adamantyl, octahydronaphthyl, decalin, camphor, camphane, and noradamantyl.

The term "direct bond" means that the group can be nothing.

The terms "effective amount" and "effective use level" of hybrid polymer refer to a sufficient amount of hybrid polymer employed to provide desired performance attributes, stability, efficacy, product aesthetics, and the like.

The term "ether" refers to a compound containing an oxygen atom connected to two alkyl or aryl groups. The term "cyclic ether" refers to an ether compound in which the oxygen group is a member of a ring. Non-limiting examples of cyclic ethers include:

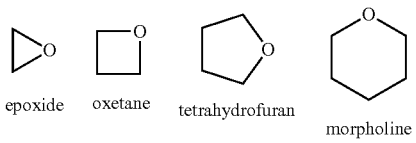

epoxide   oxetane   tetrahydrofuran   morpholine

The term "free radical addition polymerization initiator" refers to a compound used in a catalytic amount to initiate a free radical addition polymerization, and is used herein as simply "initiator"". The term "free radical addition polymerization initiator" also refers to thermal and light activated initiators. The choice of "initiator" depends mainly upon its solubility and its decomposition temperature.

The term "functionalized" refers to the state of a moiety that has one or more functional groups introduced to it by way of one or more functionalization reactions known to a person having ordinary skill in the art. Particular, yet non-limiting examples of functionalization reactions include epoxidation, sulfonation, hydrolysis, amidation, esterification, hydroxylation, dihyroxylation, amination, ammonolysis, acylation, nitration, oxidation, dehydration, elimination, hydration, dehydrogenation, hydrogenation, acetalization, halogenation, dehydrohalogenation, Michael addition, aldol condensation, Canizzaro reaction, Mannich reaction, Clasien condensation, Suzuki coupling, and the like. Particularly, functionalization of a moiety replaces one or more hydrogens in the moiety with one or more non-hydrogen groups, for e.g., alkyl, alkoxyl, cycloalkyl, alkenyl, cycloalkenyl, alkynyl, and/or aryl groups. Particular, yet non-limiting examples of cycloalkyl groups include cyclopentane, cyclohexane, cycloheptane, and the like. Particular, yet non-limiting examples of alkoxy groups include methoxy, ethoxy, n-propoxy, isopropoxy, and the like. Particular, yet non-limiting examples of aryl groups include benzenes, naphthalenes (2 rings), anthracenes (3 rings), and the like.

The term "functional group" refers to a moiety such as carboxylic acid, amide, ester, ketone, aldehyde, alcohol, halogen, amine, and the like.

The term "halogen" refers to chloro, bromo, iodo and fluoro. In one embodiment, the halogen is bromo and/or chloro.

The term "heteroatom" refers to atoms such as oxygen, nitrogen, sulfur, silicon, phosphorous, and/or halogen. The heteroatom(s) may be present as a part of one or more heteroatom-containing functional groups and/or as a part of one or more heterocyclic rings. Non-limiting examples of heteroatom-containing functional groups include ether, hydroxy, epoxy, carbonyl, carboxamide, carboxylic ester, carboxylic acid, imine, imide, amine, sulfonic, sulfonamide, phosphonic, and silane groups.

The term "homopolymer" refers to a molecule that comprises one type of monomer and the term "non-homopolymer" refers to a polymer that comprises more than one type of monomer and includes such polymers wherein a small amount of polymerization solvent may or may not be covalently bonded into the polymer. The non-homopolymer may be a copolymer, terpolymer, tetramer, or the like.

The term "hybrid polymer" refers to a polymer comprising a cellulose ether moiety, a linking group moiety, a spacer group moiety, and a lactam moiety.

The term "is derived from" refers to a compound that is obtained from another compound. For example, the term "$L_1$ is a linking group moiety . . . derived from a moiety selected from the group consisting anhydrides, cyclic ethers, and aziridines" means that the linking group $L_1$, as present in the hybrid polymer, is obtained from another compound, namely from anhydrides, cyclic ethers, and aziridines, respectively.

The terms "linking group" and "spacer group" refer to a segment or group of molecules configured to connect two or more molecules to each another. When the linking group or spacer group is defined as being absent, the linking group or spacer group is replaced by a direct bond.

The term "monomer" refers to the repeat units that comprise a polymer. A monomer is a compound that chemically bonds to other molecules, including other monomers, to form a polymer.

The term "multifunctional" refers to compounds having multiple or many functions or activities.

The term "one embodiment," "one aspect", "one version", and "one objective" of the invention include one or more such embodiments, aspects, versions, or objectives, unless the context clearly dictates otherwise.

The term "personal care composition" refers to such illustrative non-limiting compositions as skin, sun, oil, hair, and preservative compositions, including those to alter the color and appearance of the skin.

The term "pH" refers to a measure of the acidity or basicity of an aqueous solution. Pure water is considered to be neutral, with a pH of about 7.0 at 25° C. Solutions with a pH less than 7 are considered to be acidic and solutions with a pH greater than 7 are considered to be basic or alkaline.

The terms "pharmaceutically acceptable" and "cosmetically acceptable" refer to molecular entities and compositions that are generally regarded as safe. Particularly, as used herein, the term "pharmaceutically acceptable" and "cosmetically acceptable" refer to approved by a regulatory agency of the appropriate governmental agency or listed in the U.S. Pharmacopoeia or other generally recognized pharmacopoeia for use in animals, and more particularly in humans.

The term "pharmaceutically acceptable excipient" refers to an additive included in a solid formulations in the form of powders, granules, capsules, pellets and tablets to increase the bulk of the desired formulation comprising present solid dispersion. The excipients may be added during or after the preparation of solid dispersion using spray drying or hot-melt extrusion or other methods.

The term "pharmaceutically active ingredient" refers to any ingredient considered to have a therapeutic effect when delivered to a subject in need thereof and further being regulated by drug authorities. Pharmaceutically active ingredients may act systemically upon oral consumption, or locally such as when present in the buccal cavity, on the skin, etc. They may also be delivered across the skin as in transdermal drug delivery systems.

The term "polymer" refers to both linear and branched polymers derived from one or more monomer units, which may or may not be crosslinked or grafted. Non-limiting examples of polymers include copolymers, terpolymers, tetramers, and the like, wherein the polymer is random, block, or alternating polymer.

The term "poorly soluble" refers to slightly soluble or very slightly soluble compounds that require from about 100 or more parts of solvent for one part of solute. The poorly soluble compound means that the solubilization of the active pharmaceutical ingredient (API) compound becomes the rate-limiting step for absorption of such API compound.

The term "preferred," "preferably", and variants thereof, refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The hybrid polymers in the present invention are polymers comprising a cellulose ether moiety covalently bonded to a lactam moiety via a linking group moiety and a spacer group moiety.

While the carbonyl oxygen atom in lactam moieties, such as polyvinylpyrrolidone, is a strong hydrogen bond accepter, access to the oxygen atom is hindered due to the close proximity of the oxygen atom to the polymeric backbone. This steric hindrance can make it difficult to prepare polymers comprising both lactam moieties and cellulose ethers. Applicants have found that extending the lactam moiety, or polyvinylpyrrolidone group, away from the polymeric backbone on a pendant linking group/spacer group moiety results in less steric hindrance and better access to the lactam oxygen atom. By employing a pendant linking group/spacer group moiety, lactam moieties and cellulose ethers can be readily combined into hybrid polymers having the desirable properties of both groups.

Cellulose is a naturally available polymer of β-glucose linked together via β(1→4) glycosidic bonds. Cellulose is commonly found in plant cell walls and is responsible for cell wall rigidity because enhanced tensile strength of cellulose is derived from strong hydrogen bonding interactions between adjacent polymer chains. Hydrogen bonding between such polysaccharides can be weakened with various chemical modifications. For example, many functional groups (e.g. alkyl groups or ester groups) on cellulose ethers (or esters) can result in a reduced number of hydroxy groups and the physical separation between the chains can cause hydrogen bonding between the polysaccharides to be weakened. Such structurally modified cellulose products are capable of providing a material having different new properties compared to original natural cellulose. Such modified cellulose can be employed in various applications including but not limited to pharmaceuticals, food and beverages, coatings, paints, oil and energy sectors, performance materials, oral care, skin care, hair care, cosmetics, toiletry, household and cleaning products, industrial and institutional cleaning products, disinfecting products, opthalmics, injectables, sanitary products, agricultural products, textiles, biocides, preservatives, consumer products, and/or laundry products. Hybrid polymers are capable of providing very desirable functional properties having both cellulose and lactam chemistries, thus providing enhanced application performance in various fields.

In a first embodiment, the hybrid polymer has the structure:

$$A\text{-}(L_1\text{-}X\text{---}(B)_k)_q$$

wherein A is derived from a cellulose ether moiety comprising a —OH group;
$L_1$ is a linking group moiety selected from the group consisting of urethanes, amides, esters, carbonates, and phosphate esters, or is derived from a moiety selected from the group consisting of anhydrides, cyclic ethers, and aziridines; X is a spacer group moiety, selected from the group consisting of straight- or branched-chain functionalized and unfunctionalized alkyl, cycloalkyl, alkenyl, and aryl groups, wherein any of the above groups may be with or without heteroatoms, or is a direct bond; and
B is a lactam moiety;
wherein k≥1 and q≥1.

Preferably, A has the structure:

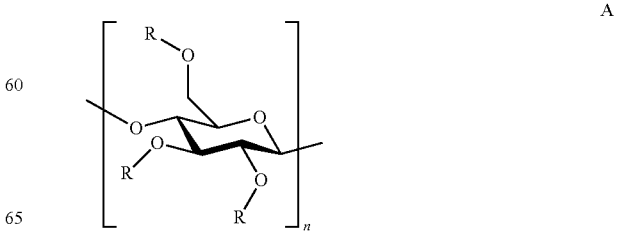

wherein R is independently selected from the group consisting of (i) hydrogen; (ii) $C_1$ to $C_{50}$ straight- or branched-chain functionalized or unfunctionalized alkyl, cycloalkyl, aryl, cycloaryl, alkoxy, aryloxy, cycloalkoxy, cycloaryloxy groups; (iii) hydroxyalkyl functional groups; (iv) alkylcarboxy groups; and (v) functionalized and non-functionalized, substituted or free carbonyl groups; wherein the above functional groups may be with or without heteroatoms; and n is from 1 to about 2000; wherein at least one R is covalently bonded to a lactam group moiety, via a linking group moiety and spacer group moiety, respectively.

More preferably, the cellulose ether moiety A is selected from the group consisting of methylcellulose, ethylcellulose, methyl(hydroxyethyl) cellulose, hydroxyethyl cellulose, hydrophobically modified hydroxyethyl cellulose, carboxymethyl hydroxyethyl cellulose, carboxymethyl cellulose, hydroxypropyl methyl cellulose, ethyl(hydroxyethyl) cellulose, and hydroxypropylcellulose.

Most preferably, the cellulose ether moiety A is selected from the group consisting of methylcellulose, carboxymethyl cellulose, hydroxyethyl cellulose, and hydroxypropyl methylcellulose.

In one aspect, the linking group moiety $L_1$ is derived from a cyclic ether. In another aspect, the linking group moiety $L_1$ is an amide or is derived from an anhydride.

The X spacer group moiety may be selected from the group consisting of $C_1$ to $C_{50}$ straight- or branched-chain functionalized and unfunctionalized alkyl, cycloalkyl, alkenyl, and aryl groups, wherein any of the above groups may be with or without heteroatoms.

Preferably, the lactam moiety B has the following structure:

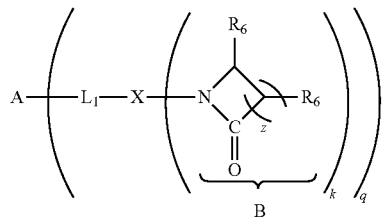

wherein $R_6$ is selected from the group consisting of hydrogen, optionally one or more functional groups, functionalized and unfunctionalized alkyl, cycloalkyl, alkenyl, and aryl groups; and mixtures thereof; wherein z=0 to 4. The variables k, q, A, $L_1$, and X are defined as set out above.

More preferably, the lactam moiety B is selected from the group consisting of a-lactam (α-aziridinone), β-lactam (β-propiolactam), γ-lactam (γ-butyrolactam), δ-lactam (δ-valerolactam), and ε-lactam (ε-caprolactam).

In a preferred embodiment, the hybrid polymer is the product derived from the chemical reaction of A, wherein A is derived from a cellulose ether moiety comprising a —OH group, wherein the structure of A is set out below:

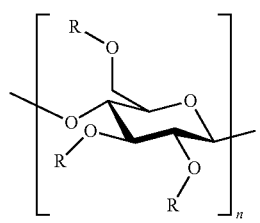

wherein R is independently selected from the group consisting of (i) hydrogen; (ii) $C_1$ to $C_{50}$ straight- or branched-chain functionalized or unfunctionalized alkyl, cycloalkyl, aryl, cycloaryl, alkoxy, aryloxy, cycloalkoxy, cycloaryloxy groups; (iii) hydroxyalkyl functional groups; (iv) alkylcarboxy groups; and (v) functionalized and non-functionalized, substituted or free carbonyl groups; wherein the above functional groups may be with or without heteroatoms; and n is from 1 to about 2000; wherein at least one R is covalently bonded to a lactam group moiety, via a linking group moiety and spacer group moiety, respectively;
and Q, wherein the structure of Q is set out below:

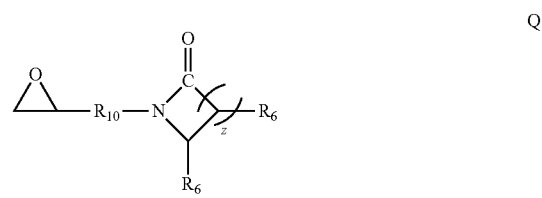

wherein $R_6$ is selected from the group consisting of hydrogen, optionally one or more functional groups, functionalized and unfunctionalized alkyl, cycloalkyl, alkenyl, and aryl groups; and mixtures thereof; wherein z=0 to 4; $R_{10}$ is selected from the group consisting of straight- or branched-chain functionalized and unfunctionalized alkyl, cycloalkyl, alkenyl, and aryl groups, wherein any of the above groups may be with or without heteroatoms, or is a direct bond; wherein z=0 to 4.

In a second embodiment, the hybrid polymer has the structure:

$$A\text{-}(L_2\text{-}X\text{—}B)_y$$

wherein A is derived from a cellulose ether moiety comprising a —OH group;
$L_2$ is an ether linking group moiety;
X is a spacer group moiety, selected from the group consisting of straight- or branched-chain functionalized and unfunctionalized alkyl, cycloalkyl, alkenyl, and aryl groups, wherein any of the above groups may be with or without heteroatoms, or is a direct bond; and B is a lactam moiety; wherein y≥1;
with the proviso that when the cellulose ether moiety is hydroxyethyl cellulose,-$(L_2\text{-}X\text{—}B)_y$, is not derived from 1-(hydroxymethyl)-2-pyrrolidinone.

Preferably, A has the structure:

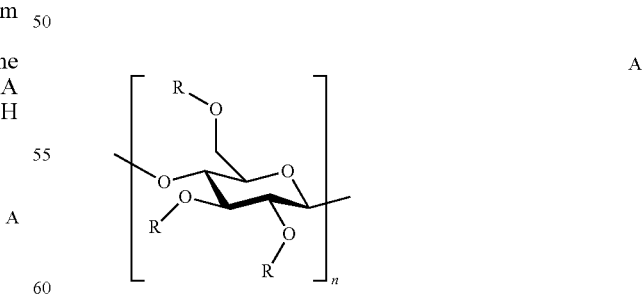

wherein R is independently selected from the group consisting of (i) hydrogen; (ii) $C_1$ to $C_{50}$ straight- or branched-chain functionalized or unfunctionalized alkyl, cycloalkyl, aryl, cycloaryl, alkoxy, aryloxy, cycloalkoxy, cycloaryloxy groups; (iii) hydroxyalkyl functional groups: (iv) alkylcarboxy groups; and (v) functionalized and non-functionalized, substituted or free carbonyl groups; wherein the above functional groups may be with or without heteroatoms; and n is from 1 to about 2000; wherein at least one R is covalently bonded to a lactam group moiety, via a linking group moiety and spacer group moiety, respectively.

More preferably, the cellulose ether moiety A is selected from the group consisting of methylcellulose, ethylcellulose, methyl(hydroxyethyl) cellulose, hydroxyethyl cellulose, hydrophobically modified hydroxyethyl cellulose, carboxymethyl hydroxyethyl cellulose, carboxymethyl cellulose, hydroxypropyl methyl cellulose, ethyl(hydroxyethyl) cellulose, and hydroxypropylcellulose.

Most preferably, the cellulose ether moiety A is selected from the group consisting of methylcellulose, carboxymethyl cellulose, hydroxyethyl cellulose, and hydroxypropyl methylcellulose.

The X spacer group moiety may be selected from the group consisting of $C_1$ to $C_{50}$ straight- or branched-chain functionalized and unfunctionalized alkyl, cycloalkyl, alkenyl, and aryl groups, wherein any of the above groups may be with or without heteroatoms.

Preferably, lactam moiety B has the structure:

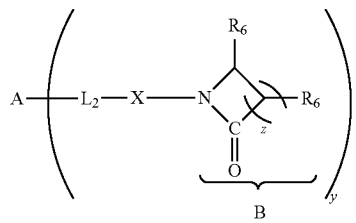

wherein $R_6$ is selected from the group consisting of hydrogen, optionally one or more functional groups, functionalized and unfunctionalized alkyl, cycloalkyl, alkenyl, and aryl groups; and mixtures thereof; wherein z=0 to 4. The variables y, A, $L_2$, and X are defined as set out above.

More preferably, the lactam moiety B is selected from the group consisting of a-lactam (α-aziridinone), β-lactam (µ-propiolactam), γ-lactam (γ-butyrolactam), δ-lactam (δ-valerolactam), and ε-lactam (ε-caprolactam).

The present invention also provides a composition comprising a hybrid polymer having the structure:

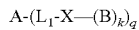

wherein A is derived from a cellulose ether moiety comprising a —OH group;
$L_1$ is a linking group moiety selected from the group consisting of urethanes, amides, esters, carbonates, and phosphate esters, or is derived from a moiety selected from the group consisting anhydrides, cyclic ethers, and aziridines;
X is a spacer group moiety, selected from the group consisting of straight- or branched-chain functionalized and unfunctionalized alkyl, cycloalkyl, alkenyl, and aryl groups, wherein any of the above groups may be with or without heteroatoms, or is a direct bond; and
B is a lactam moiety;
wherein k≥1 and q≥1.

The present invention further provides a composition comprising a hybrid polymer having the structure:

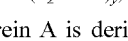

wherein A is derived from a cellulose ether moiety comprising a —OH group;

$L_2$ is an ether linking group moiety;
X is a spacer group moiety, selected from the group consisting of straight- or branched-chain functionalized and unfunctionalized alkyl, cycloalkyl, alkenyl, and aryl groups, wherein any of the above groups may be with or without heteroatoms, or is a direct bond; and
B is a lactam moiety;
wherein y≥1;
with the proviso that when the cellulose ether moiety is hydroxyethyl cellulose, $-(L_2-S-B)_y$ is not derived from 1-(hydroxymethyl)-2-pyrrolidinone.

According to a non-limiting embodiment of the present application, suitable cellulose ether moieties include hydroxyalkyl celluloses, alkyl celluloses, carboxyalkyl celluloses, for example, methyl cellulose (MC), ethylcellulose (EC), propyl cellulose (PC), methylhydroxyethylcellulose (MHEC), ethyl hydroxyethyl cellulose (EHEC), methylethyl hydroxyethyl cellulose (MEHEC), hydroxypropyl hydroxyethyl cellulose (HPHEC), methyl hydroxypropyl hydroxyethyl cellulose (MHPHEC), hydroxypropyl cellulose (HPC), methyl hydroxypropyl cellulose (MHPC), and ethyl hydroxypropyl cellulose (EHPC), hydroxypropyl methyl cellulose (HPMC), ethylhydroxyethylcellulose (EHEC), carboxyalkylcelluloses, carboxyalkylhydroxyalkylcellulose, carboxymethyl cellulose, carboxymethylcellulose, and carboxypropylcellulose. Preferred cellulose ether moieties are methylcellulose (MC), ethylcellulose (EC), methylhydroxyethylcellulose (MHEC), hydroxypropyl methyl cellulose (HPMC) and ethylhydroxyethylcellulose (EHEC), and methylhydroxyethylcellulose (MHEC).

According to another aspect of the present application, cellulose ethers, for example, HPMC, HPC having a molecular weight range of 15,000 to 200,000 g/mol, react with pyrrolidone containing reagents, for example, I-hydroxymethyl-2-pyrrolidone (HMP), N-glycidyl pyrrolidone (NGP) and ethylpyrrolidone glycidyl ether (EPGE), I-hydroxymethyl-2-caprolactone, epoxypropyl pyrrolidone (EPP) and pyrrolidinonyl ethylglycidyl ether (PEGE) to provide novel cellulose ether polymers containing pendant pyrrolidone functionality with a molar substitution (MS) ranging from 0.1 to 5.0, dependent on the initial level of ether capping on the starting cellulose ether as well as the stoichiometry of the pyrrolidone containing reagent relative to the level of free hydroxyl groups present on the cellulose ether.

According to another embodiment of the present application, certain cellulose ethers, for example, methyl cellulose (MC) and HPMC, having a range of molecular weight of about 10,000 to 200,000 g/mol, react with pyrrolidone containing reagents, for example, 1-hydroxynethyl-2-pyrrolidone (HMP), N-glycidyl pyrrolidone (NGP) and ethylpyrrolidone glycidyl ether (EPGE), 1-hydroxymethyl-2-caprolactone, epoxypropyl pyrrolidone (EPP) and pyrrolidinonyl ethylglycidyl ether (PEGE) in conjunction with esterifying agents, for example, various acyl halides (R—CO—Cl) or anhydrides (R—(C=O)—O—(CO)—R), to provide novel cellulose ether-ester polymers containing pendant pyrrolidone functionality where the sum of the ester and pyrrolidone MS ranges from 0.1 to 5.0, dependent on the initial level of ether capping on the starting cellulose ether as well as the stoichiometry of the esterifying and lactam containing reagents relative to the level of free hydroxyl groups present on the cellulose ether. The esterifying agent can be chosen from reagents which will produce a cellulose alkonate where the alkonate group is chosen from, but not limited to, acetate, proprionate, butyrate, succinate, maleate, phthalate, citrate, and trimellitate, wherein the lactam is selected from the group as described above, particularly, substituted or non-substituted lactam ring having Cps.

The unexpected properties achieved by combining cellulose ether-ester chemistry with substituted or non-substituted lactam functionality include greater amphiphilic properties (such as when the alkonate group is chosen from acetate, proprionate or butyrate) as well improved control of pH dependent solubility (such as when the alkonate group is chosen from phthalate, succinate, maleate, citrate or trimellitate).

The preferred molecular weight of the cellulose ether lactam hybrid polymer is in the range from about 10,000 to about 1,000,000. In another preferred embodiment, the molecular weight of the cellulose ether lactam hybrid polymer is in the range from about 100,000 to about 1,000,000, more preferably, from about 200,000 to about 1,000,000, and most preferably, from about 300,000 to about 1,000,000. In another preferred embodiment, the molecular weight of the cellulose ether lactam hybrid polymer is in the range from about 10,000 to about 900,000, more preferably, from about 10,000 to about 800,000, and most preferably, from about 10,000 to about 700,000.

The cellulose ether lactam hybrid polymers of the present invention may be employed with various active agents to provide many compositions having various end-user applications including, but not limited to, pharmaceuticals, food and beverages, coatings, paints, oil and energy sectors, performance materials, oral care, skin care, hair care, cosmetics, toiletry, household and cleaning products, industrial and institutional cleaning products, disinfecting products, opthalmics, injectables, sanitary products, agricultural products, textiles, biocides, preservatives, consumer products, and laundry products.

Personal care and cosmetic active agents may be employed in the inventive compositions such as those agents selected from the group consisting of allantoin, tocopherol nicotinate, niacinamide, retinyl propionate, palmitoyl-gly-his-lys, phytosterol, isoflavone, dexpanthenol, panthenol, bisabolol, farnesol, phytantriol, salicylic acid, zinc/sodium pyridinethione salts, piroctone olamine, selenium disulfide, tetrahydrocurcumin, glucosamine, N-actyl glucosamine, vitamin B3, retinoids, peptides, phytosterol, dialkanoyl hydroxyproline, hexamidine, salicylic acid, N-acyl amino acids, escolols, sunscreen actives, UV-A/UV-B protecting agent, water soluble vitamins, oil soluble vitamins, hesperedin, mustard seed extract, glycyrrhizic acid, glycyrrhetinic acid, carnosine, butylated hydroxytoluene (BHT) and butylated hydroxyanisole (BHA), ergothioneine, vanillin, vanillin derivatives, diethylhexyl syrinylidene malonate, melanostatine, sterol esters, fatty acids, poly-unsaturated fatty acids, zinc pyrithione (ZPT), anti-fungal agents, thiol compords, N-acetyl cysteine, glutathione, thioglycolate, β-carotene, ubiquinone, amino acids, idebenone, dehydroacetic acid, licohalcone A, creatine, creatinine, feverfew extract, yeast extract, β-glucans. α-glucans, and mixtures thereof.

Personal care compositions may be prepared by employing a personal care or cosmetic agent such as those selected from the group consisting of fatty substances, gelling agents, thickeners, surfactants, moisturizers, emollients, hydrophilic or lipophilic active agent, antioxidants, sequestering agents, preserving agents, acidifying or basifying agents, fragrances, fillers, dyestuffs, emulsifying agents, solvents, UV-A or UV-B blocker/filters, plant extracts, moisturizers, proteins, peptides, neutralizing agents, solvents, silicones, and reducing agents.

Personal care compositions that can prepared employing the hybrid polymer may be selected from the group consisting of hair-care products, shampoos, hair conditioners, leave in and rinse off conditioners, styling and treating hair compositions, hair perming products, hair relaxants, hair straighteners, hair sprays and lacquers, permanent hair dyeing systems, hair styling mousses, hair gels, semi-permanent hair dyeing systems, temporary hair dyeing systems, hair bleaching systems, permanent hair wave systems, hair setting formulations, skin-care products, bath products, shower products, liquid soaps, bar soaps, fragrances and/or odoriferous ingredients consisting preparations, dentifrices, deodorizing and antiperspirant preparations, decorative preparations, light protection formulations, shaving lotions, body oils, body lotions, body gels, treatment creams, body cleaning products, skin protection ointments, shaving and aftershave preparations, skin powders, lipsticks, nail varnishes, eye shadows, mascaras, dry and moist make-up, rouge, powders, depilatory agents, and sun care products.

The cellulose ether lactam based hybrid polymer can be advantageously formulated as as an emulsion, a suspension, an ointment, a lotion, a gel, a vesicle dispersion, a paste, a cream, a solid stick, a mousse, a shampoo, or a spray.

Pharmaceutical active agents may be employed in the inventive compositions such as those agents selected from the group consisting of analgesics, antibacterials, antifungals, antimicrobials, antibiotics, antipyretics, anti-inflammatory drugs, non-steroidal anti-inflammatory drugs (NSAIDS), chemotherapeutic drugs, hormones, anti-diabetic drugs, anti-psychiatric drugs, anti-viral drugs, anesthetic drugs, cardiovascular drugs, anti-asthmatic drugs, monoclonal antibodies, veterinary drugs, antiseptics, antimalerial drugs, mood stabilizers, oral contraceptives, stimulant drugs, tranquilizers, antacids, reflux suppressants, antiflatulents, antidopaminergics, proton pump inhibitors (PPIs), $H_2$-receptor antagonists, cytoprotectants, prostaglandin analogues, laxatives, antispasmodics, antidiarrhoeals, bile acid sequestrants, opioids, β-receptor blockers, calcium channel blockers, diuretics, cardiac glycosides, antiarrhythmics, nitrate, antianginals, vasoconstrictors, vasodilators, ACE inhibitors, angiotensin receptor blockers, α-blockers, thiazide diuretics, loop diuretics, aldosterone inhibitors, anticoagulants, heparin, antiplatelet drugs, fibrinolytics, anti-hemophilic factors, haemostatic drugs, HMG-CoA reductase inhibitors, hypolipidaemic drugs, psychedelics, hypnotics, antipsychotics, antidepressants, antiemetics, anticonvulsants, anxiolytics, barbiturates, movement disorder drugs, benzodiazepines, cyclopyrrolones, dopamine antagonists, antihistamines, cholinergics, anticholinergics, emetics, cannabinoids, and 5-HT (serotonin) antagonists, muscle relaxants, neuromuscular drugs, anticholinesterases, astringents, ocular lubricants, topical anesthetics, sympathominimetics, parasympatholytics, mydriatics, cycloplegics, topical antibiotics, sulfa drugs, aminoglycosides, fluoroquinolones, corticosteroids, mast cell inhibitors, adrenergic agonists, carbonic anhydrase inhibitors, hyperosmotics, cholinergics, miotics, parasympathomimetics, prostaglandin agonists/prostaglandin inhibitors, sympathomimetics, antihistamines, local anesthetics, bronchodilators, antitussives, mucolytics, decongestants, systemic corticosteroids, β2-adrenergic agonists, anticholinergics, leukotriene antagonists, androgens, antiandrogens, gonadotropin, corticosteroids, human growth hormone, insulin, thyroid hormones, antithyroid drugs, alkalinizing agents, quinolones, antispasmodics, 5-α-reductase inhibitors, selective alpha–1 blockers, sildenafils, fertility and anti-fertility drugs, spermicides, haemostatic drugs, hormone replacement therapy (HRT), bone regulators, follicle stimulating hormones, luteinising hormones, gonadotropin release inhibitor, progestrogen, dopamine agonists, oestrogen, prostaglandins, gonadorelins, emollients, anti-pruritics, disinfectants, scabicides, pediculicides, tar products, vitamins and their analogues, keratolytics, proteolytics, sunscreens, antiperspirants, corticosteroids, immune modulators, antileprotics, antituberculous drugs, anthelmintics, amoebicides, antiprotozoals, vaccines, immunoglobulins, immunosuppressants, interferons, tonics, electrolytes, mineral preparations, parenteral nutritions, anti-obesity drugs, anabolic drugs, haematopoietic drugs, food product drugs, cytotoxic drugs, therapeutic antibodies, sex hormones, aromatase inhibitors, somatostatin inhibitors, recombinant interleukins, G-CSF, and erythropoietins.

In another embodiment, the cellulose ether lactam based hybrid polymers are used to enhance the solubility of poorly soluble drugs such as those are described under Biopharmaceutical Classification System (BCS) class II and/or IV. The above disclosed non-limiting Biopharmaceutical Classification System Class II and IV drugs can be a free acid, free base or neutral molecules, or in the form of an appropriate pharmaceutically acceptable salt, a pharmaceutically acceptable solvate, a pharmaceutically acceptable co-crystal, a pharmaceutically acceptable enantiomer, a pharmaceutically acceptable derivative, a pharmaceutically acceptable polymorph, pharmaceutically acceptable ester, pharmaceutically acceptable amide or a pharmaceutically acceptable prodrug thereof.

Non-limiting Biopharmaceutical Classification System Class II drugs include Albendazole, Acyclovir, Azithromycin, Cefdinir, Cefuroxime axetil, Chloroquine, Clarithromycin, Clofazimine, Diloxanide, Efavirenz, Fluconazole, Griseofulvin, Indinavir, Itraconazole, Ketoconalzole, Lopinavir, Mebendazole, Nelfinavir, Nevirapine, Niclosamide, Praziquantel, Pyrantel, Pyrimethamine, Quinine, Ritonavir, Bicalutamide, Cyproterone, Gefitinib, Imatinib, Tamoxifen, Cyclosporine, Mycophenolate mofetil, Tacrolimus. Acetazolamide, Atorvastatin, Benidipine, Candesartan cilexetil, Carvedilol, Cilostazol, Clopidogrel, Ethylicosapentate, Ezetimibe, Fenofibrate, Irbesartan, Manidipine, Nifedipine, Nisoldipine, Simvastatin. Spironolactone, Telmisartan, Ticlopidine, Valsartan, Verapamil, Warfarin, Acetaminophen, Amisulpride, Aripiprazole, Carbamazepine, Celecoxib, Chlorpromazine, Clozapine, Diazepam, Diclofenac, Flurbiprofen, Haloperidol, Ibuprofen, Ketoprofen, Lamotrigine, Levodopa, Lorazepam, Meloxicam, Metaxalone, Methylphenidate, Metoclopramide, Nicergoline, Naproxen, Olanzapine, Oxcarbazepine, Phenyloin, Quetiapine, Risperidone, Rofecoxib, Valproic acid, Isotretinoin, Dexamethasone, Danazol, Epalrestat, Gliclazide, Glimepiride, Glipizide, Glyburide (glibenclamide), levothyroxine sodium, Medroxyprogesterone, Pioglitazone, Raloxifene, Mosapride, Orlistat, Cisapride, Rebamipide, Sulfasalazine, Teprenone, Ursodeoxycholic Acid, Ebastine, Hydroxyzine, Loratadine, and Pranlukast.

The novel cellulose ether lactam based hybrid polymers of the present application possess unexpected properties including lower glass transition temperature (Tg), unique gelation and film properties, and differentiated organic solubility. These changes in physical chemical properties translate into improved application performance in areas such as pharmaceutical and personal care applications, particularly with regard to pharmaceutical drug solubilization of solid drug dispersions (SDD) formed through spray drying or hot melt extrusion (HME) method of processing ability as well as better excipients for tablet binding and tablet coating functions.

The pharmaceutical compositions can be formulated as solids, semi-solids, liquids, gels, powders, granules, lozengens, tablets, patches, capsules, ointments, lotions, creams, suppositories, aerosols, syrups, elixirs, emulsions, non-aqueous suspensions, aqueous suspensions, and/or solutions. The pharmaceutical compositions can be administered through enteral/oral, topical, parenteral, and/or inhalation techniques.

The pharmaceutically acceptable excipients may be selected from the group consisting of plasticizers, disintegrants, surfactants, lubricants, glidants, carriers, anti-adherents, fillers, wetting agents, pH modifiers, binders, solubility modifiers, recrystallization inhibitors, coating agents, diluents, coloring agents, preservatives, antifoaming agent, antioxidants, buffering agents, acidifying agents, alkalizing agents, complexation-enhancing agent, cryoprotectant, electrolytes, gelling agents, emulsifying agents, solubility-enhancing agents, stabilizers, tonicity modifiers, flavors, sweeteners, complexing agents, fragrances, and viscosity modifiers.

The unexpected properties achieved by combining cellulose ether moieties with polyvinylpyrrolidone include greater amphiphilic properties (if the alkonate group is chosen from acetate, proprionate or butyrate) as well improved control of pH dependant solubility (if the alkonate group is chosen from phthalate, succinate, maleate, citrate or trimellitate).

According to yet another embodiment of the present application, the degree of substitution (DS) or molar substitution (MS) is in the range of from about 0.01 to about 2.0. Other non-limiting DS or MS suitable for the present invention is from about 0.01 to about 0.1, about 0.1 to about 0.2, about 0.2 to about 0.4, about 0.4 to about 0.6, about 0.6 to about 0.8, about 0.8 to about 1.0, about 1.0 to about 1.2, about 1.2 to about 1.4, about 1.4 to about 1.6, about 1.6 to about 1.8, or about 1.8 to about 2.0.

Molecular weight of the cellulose ether lactam hybrid polymer is in the range of from about 10,000 to about 1,000,000. Other preferred molecular weight ranges would include but not limited to about 10,000 to about 100,000; about 100,000 to about 200,000; about 200,000 to about 300,000; about 300,000 to about 400,000; about 400,000 to about 500,000; about 500,000 to about 600,000; about 600,000 to about 700,000; about 700,000 to about 800,000; about 800,000 to about 900,000; and/or about 900,000 to about 1000,000.

The hybrid polymer products of the present application have unexpected properties such as employing the polymer to provide lower glass transition temperature (Tg), unique gelation and film properties, and differentiated organic solubility. These changes in physical chemical properties will translate into improved application performance in areas such as pharmaceutical and personal care applications, particularly with regard to pharmaceutical drug solubilization of solid drug dispersions (SDD) formed through spray drying or hot melt extrusion (HME) method of processing ability as well as an can behave as better excipient for tablet binding and tablet coating functions.

The pharmaceutical composition prepared in accordance with the present application can be administered through enteral/oral, topical, parenteral, and/or inhalation, and wherein, the pharmaceutical composition can be formulated as solids, semi-solids, liquids, gels, powders, granules, lozenges, tablets, patches, capsules, ointments, lotions, creams, suppositories, aerosols, syrups, elixirs, emulsions, non-aqueous suspensions, aqueous suspensions, and/or solutions.

The novel hybrid polymers of the invention can be prepared according to the examples set out below. The examples are presented for purposes of demonstrating, but not limiting, the preparation of the hybrid polymers of this invention.

EXAMPLES

The following non-limiting examples are provided to illustrate the novel hybrid polymers having unique functional properties of the present invention. The present invention also provides compositions comprising the hybrid polymers and methods for preparing and using the hybrid polymers.

The following cellulose ether starting materials were used in the synthesis of Examples 1-8.

| Cellulose Ether Starting Materials for HPMC and MC Hybrid Polymers | | | |
|---|---|---|---|
| Cellulose Ether Starting Material | SEC $M_n$ (g/mol) | SEC $M_w$ (g/mol) | Tg (° C.) |
| Benecel ™ E5 HPMC | 8,000 | 31,900 | 128.9 |
| Benecel ™ E15 HPMC | 13,700 | 65,500 | 147.1 |
| Benecel ™ E50 HPMC | 25,100 | 130,000 | n.d. |
| AnyCoat C AN5 HPMC | 8,910 | 32,600 | 143.3 | n.d. = not determined

Example 1

Reaction of Hydroxypropyl Methylcellulose (HPMC) with 1-Hydroxymethyl-2-Pyrrolidone (HMP) by Melt Process General Procedure: 1-hydroxymethyl-2-pyrrolidone (HMP, 5.60 g, 48.6 mmol) and HPMC (Benecel™ E15, 1.0 g, 4.9 mmol) were combined in a 50 mL round-bottom flask. 2-amino-2-methyl-1-propanol hydrochloride (AMPHC, 0.186 g, 1.48 mml) was added and the flask flushed with nitrogen for 5 min. The flask was fitted with a rubber septum and vented to an oil bubbler. The mixture was heated to 130° C. and held for 3 h. The orange, viscous reaction mixture was allowed to cool to ambient temperature and diluted with 25 mL of acetone. This slurry was mixed and then placed on a roto-evaporator to remove all volatiles. The crude material was dissolved in 15 mL deionized water. The solution was transferred to a dialysis membrane pouch (Spectra/Por®, MW cut-off 3,500 g/mol), sealed and the pouch suspended in a beaker containing 2 L of deionized water. The dialysis pouch was stirred in the water for 1 day. The water was discarded, and an additional 2 L of water was charged, and stirring continued for another day. The contents of the dialysis membrane pouch were transferred to a round-bottom flask and frozen over a dry ice/acetone bath. The frozen solution was lyophilized Dialysis Membrane Protocol: Spectra/Por® MWCO 3.5K Regenerated Cellulose (RC) dialysis membranes were purchased from Spectrum Labs (spectrumlabs.corn, Flat With=45 mm, Diameter=29 mm, Volume/Length=6.4 mL/cm, Part #132111). A dialysis pouch is formed by first cutting a small length (~10 cm) of membrane from the roll and swelling the membrane in water to open the tube. One end of the tube is sealed using a Universal Closure clip (Yellow, 50 mm, Part #142153). The pouch is then filled with a 10-50% w/w aqueous solution (20 mL) of the impure polymer material in deionized water. The pouch is sealed with another Universal Closure, and the pouch suspended in a 2 L beaker of water containing a large Teflon stir bar. The beaker is placed on a stir plate, and stirring commenced at such a rate to allow the suspended membrane pouch to rotate slowly within the vortex. The dialysis is allowed to continue for 72 h, at which point the beaker water is decanted and replaced with an additional 2 L of water. The dialysis was continued as before for an additional 24 h. The contents of the membrane pouch are then transferred to a round-bottom flask and frozen using a dry/ice acetone bath. The flask containing the frozen mixture is then freeze-dried using a lyopholizer until a dry solid is obtained.

The following sample was prepared according to the method set out in Example 1.

| Sample | Sample Description/Purification | SEC $M_n$ (g/mol) | SEC $M_w$ (g/mol) | Tg (° C.) |
|---|---|---|---|---|
| 75 | HPMC-MP Synthesis with Benecel ™ E15 HPMC (Dialysis/Lyopholization Purification) | 6,050 | 24,500 | 120.3 |

Example 2

Hydroxypropyl Methylcellulose-Methylpyrrolidone (HPMC-MP) Polymers Prepared by Reaction in Toluene General Procedure: Toluene (501.3 g) was charged to a 2 L kettle reactor fitted with overhead stirrer, agitator, thermoprobe, Dean-Stark trap (containing pre-dried 4A molecular sieves) and condenser with nitrogen inlet/outlet. HPMC (Benecel™ E5, 50.2 g, 245 mmol), HMP (57.6 g, 500 mmol), and 2-amino-2-methyl-1-propanol hydrochloride (4.53 g, 36.0 mmol) were added sequentially to the reactor kettle. The mixture was sparged with nitrogen for several minutes with stirring at 300 RPM. The sparge was replaced with a nitrogen blanket, and the reaction mixture heated to 110° C. Heating at reflux was continued for 3 h. The orange solution was allowed to cool to ambient temperature before adding hexane (140 g) to precipitate an orange solid. Stirring was ceased, and the solids allowed to settle prior to decanting off the solvent. The solid was washed with two additional portions of hexane (140 g each) to give an orange solid that was allowed to air dry. The dried solid was added to water (400 g) in a 1 L kettle reactor and dispersed with a high-sheer impeller agitator. The heterogeneous mixture was warmed to 70° C. until a loose solid precipitate formed. This process was repeated two additional times with 500 mL water leaving a soft, yellow solid. This material was allowed to air dry overnight, prior to further drying in a vacuum oven at 80° C.

Additional HPMC-MP samples were prepared according to the method set out in Example 2.

| Sample | Sample Description/Purification | SEC $M_n$ (g/mol) | SEC $M_w$ (g/mol) | Tg (° C.) |
|---|---|---|---|---|
| 148 | HPMC-MP Synthesis with Benecel ™ E5 HPMC in Toluene | 19,700 | 42,300 | 106.2 |
| 149 | HPMC-MP Synthesis with Benecel ™ E15 HPMC in Toluene | 25,300 | 72,800 | 97.9 |
| 151 | HPMC-MP Synthesis with Benecel ™ E50 HPMC in Toluene | 33,00 | 124,000 | 95.3 |
| 161 | HPMC-MP Synthesis with Benecel ™ E5 HPMC in Toluene | 19,900 | 43,200 | 95.8 |
| 165 | HPMC-MP Synthesis with Benecel ™ E15 HPMC in Toluene | 14,300 | 37,200 | 114.7 |

Example 3

Methylcellulose-N-Ethylpyrrolidonyl Hydroxypropoxy Ether (MC-EPGE) Polymers Prepared by Reaction in Heptane General Procedure: Heptane (80 g) was charged to a 250 mL round-bottom flask fitted with overhead stirrer with agitator, thermoprobe, and condenser with nitrogen inlet/outlet. HPMC (Benecel™ A15LV, 25.0 g, 133.6 mmol) was added and a nitrogen sparge initiated with stirring. 50% aqueous sodium hydroxide (8.6 g, 107.5 mmol) was added and the mixture stirred for 15 min. N-Ethylpyrrolidone glycidyl ether, EPGE (13.6 g, 73.5 mmol) was added and the nitrogen sparge replaced by a nitrogen blanket. The reaction was heated to 80° C. for 3 h. The heterogenous mixture was allowed to cool to ambient temperature and the solvent decanted from the brown solid. The solid was washed with two additional portions of heptane and air dried. The solid was dispersed in acetone (250 mL), and the mixture neutralized to ~pH 7 with 10% aqueous hydrochloric acid. The mixture was filtered, and the solid washed with two additional portions of acetone, neutralizing to pH 7 as needed. The resulting solid was dried at 60° C. in a fluidized bed dryer for 2 h.

The following sample was prepared according to the method set out in Example 3.

| Sample | Sample Description/Purification | SEC $M_n$ (g/mol) | SEC $M_w$ (g/mol) |
|---|---|---|---|
| 199 | MC-EPGE Synthesis with Benecel ™ A15LV MC in Heptane | 12,700 | 64,800 |

Example 4

Hydroxypropyl Methylcellulose-N-Ethylpyrrolidonyl Hydroxypropoxy Ether (HPMC-EPGE) Polymers Prepared by Reaction in t-Butanol General Procedure: t-Butanol (400 g) was charged to a 1 L kettle flask fitted with overhead stirrer with agitator, thermoprobe, and condenser with nitrogen inlet/outlet HPMC (AnyCoat-C AN5, 50.0 g, 244 mmol) was added and a nitrogen sparge initiated with stirring. 50% aqueous sodium hydroxide (9.78 g, 122 mmol NaOH) was added and the mixture stirred for 15 min. N-Ethylpyrrolidone glycidyl ether, EPGE (27.2 g, 147 mmol) was added and the nitrogen sparge replaced by a nitrogen blanket. The reaction was heated to 70° C. for 4 h. The heterogenous mixture was allowed to cool to ambient temperature and neutralized to pH ~6 with 50% aqueous acetic acid. The reaction mixture was diluted with hexane and filtered. The filter cake was washed with two additional portions of hexane. The resulting solid was air dried and then subjected to hot water precipitation and drying: The solid product was added to a 1 L kettle flask containing deionized water (500 mL) heated to 95° C. and stirring at 400 RPM using an overhead mixer fitted with an anchor agitator. After 10 min of stirring, the liquid was decanted and an additional 500 mL of deionized water was added to the flask. The mixture was warmed back to 95° C. to fully precipitate the solid, and stirred 10 min. The solid precipitate was removed from the reactor and placed in an aluminum pan. This material was dried in a vacuum oven at 70° C. for 6-10 hrs until percent solids>95%.

The following sample was prepared according to the method set out in Example 4.

| Sample | Sample Description/Purification | SEC $M_n$ (g/mol) | SEC $M_w$ (g/mol) |
|---|---|---|---|
| 9 | HPMC-EPGE Synthesis with AnyCoat-C AN5 HPMC in t-Butanol | 13,100 | 44,900 |

Example 5

Hydroxypropyl Methylcellulose-N-Hydroxypropyl-Pyrrolidonyl Ether (HPMC-EPP) Polymers Prepared by Reaction in t-Butanol This reaction was performed using the same procedure as outlined in Example 4 with EPGE being replaced with 1-(2,3-Epoxy propyl)-2-pyrrolidinone (EPP) as the pyrrolidone glycidyl ether reagent.

The following sample was prepared according to the method set out in Example 5.

| Sample | Sample Description/Purification | SEC $M_n$ (g/mol) | SEC $M_w$ (g/mol) |
|---|---|---|---|
| 199B | HPMC-EPP Synthesis with AnyCoat-C AN5 HPMC in t-Butanol | 10,100 | 40,600 |

Example 6

Hydroxypropyl Methylcellulose—N-Ethylpyrrolidonyl Hydroxypropoxy Ether Acetate (HPMC-EPGE Acetate) Polymers Prepared by Reaction in t-Butanol t-Butanol (202 g) was charged to a 500 mL round bottom flask fitted with overhead stirrer with agitator, thermoprobe, and condenser with nitrogen inlet/outlet. AnyCoat C AN5 HPMC (25 g, 124 mmol) was added and a nitrogen sparge initiate with stirring. 50% aqueous sodium hydroxide (4.88 g, 61.8 mmol NaOH) was added and the mixture stirred for 15 min. N-Ethylpyrrolidone glycidyl ether, EPGE (13.7 g, 74.1 mmol) was added and the nitrogen sparge replaced by a nitrogen blanket. The reaction was heated to 70° C. for 3 h. The reaction mixture was allowed to cool to 50° C. and acetic anhydride (12.6 g, 124 mmol) was added slowly to the reaction. The heterogenous mixture was warmed to 70° C. and stirred an additional 1 h. The reaction was allowed to cool to ambient temperature, diluted with hexane to precipitate a brown solid, and filtered. The filter cake was washed with two additional portions of hexane. The resulting solid was air dried and then subjected to hot water precipitation and drying: The solid product was added to a 1 L kettle flask containing deionized water (500 mL) and the pH of the mixture was carefully adjusted with 50% aqueous sodium hydroxide to pH 6 while stirring at 400 RPM using an overhead mixer fitted with an anchor agitator. The resulting solution was heated to 95° C. to precipitate a solid. After an additional 10 min of stirring following precipitation, the liquid was decanted and an additional 500 mL of deionized water was added to the flask. The mixture was warmed back to 95° C. to fully precipitate the solid, and stirred 10 min. The solid precipitate was removed from the reactor and placed in an aluminum pan. This material was dried in a vacuum oven at 70° C. until percent solids were >95%. The solid polymer was milled to a fine powder.

The following compound was prepared according to the method set out in Example 6.

| Sample | Sample Description/Purification | SEC $M_n$ (g/mol) | SEC $M_w$ (g/mol) |
|---|---|---|---|
| 21 | HPMC-EPGE-Acetate Synthesis with AnyCoat-C AN5 HPMC in t-Butanol | 10,100 | 40,600 |

Active Pharmaceutical Ingredient

Efavirenz is a nonnucleoside reverse transcriptase inhibitor (NNRTI) of human immunodeficiency virus type 1 (HIV-1). Efavirenz is a Biopharmaceutics Classification System II (BCS-2) type drug, with poor aqueous solubility and high permeability. The molecular weight is 315.7 Dalton. The melting temperature of Efavirenz is between 139° C.–141° C., and the glass transition temperature is around 35° C. The partition coefficient in an octanol-water system (logP) is 4.7, indicating the drug is much more lipophilic than hydrophilic.

Dispersion Preparation Process

The active pharmaceutical ingredient (API) and polymer were mixed in a 30:70 ratio and spray-dried into a spray dried dispersion (SDD). The following are the solution preparation and spray drying process information.

Solution preparation: Efavirenz and polymers were dissolved in a 2:1 (w/w) mixture of acetone:methanol solution at a total 3% solid loading. Dissolution of all components was visually confirmed before spray drying.

Spray drying: Spray drying was performed on a GEA-Niro SD Micro spray dryer. All dispersions were spray dried targeting an inlet gas temperature of 85° C., 25 kg/hour process gas flow, 0.5 barr atomization gas pressure, 1.5 kg/hour atomizing gas flow, and an adjustable liquid feed rate targeting an outlet gas temperature of 55° C. The feed solution was held at ambient conditions.

Dispersion Characterization:

Dissolution: The dissolution tests were conducted using Pion μDiss Profiler with in situ Fiber Optic UV-Vis Monitoring. 66.7 mg spray dried dispersion (SDD) was weighed and tested in the dissolution, with 30% drug loading level (20 mg API). The controlled reference used in dissolution testing is pure API Efavirenz (20 mg). The quantity of dissolution media is 20 mL. The API concentrations were monitored for 2 hours. For each sample, triplicate measurements were taken and the average results were reported.

Fasted Simulated Intestine Fluid (FaSSIF), as well as pH 6.8 phosphate buffer, were used to perform the dissolution. FaSSIF is virtually the same as the small intestinal juices present when one hasn't eaten any food, and contain bile salts and phospholipids, physiologically relevant surfactants which are missing from typical dissolution media. The use of FaSSIF media can help to better correlate the in vitro dissolution property and the in vivo response (IVIVC), so as to further understand the API performance in actual human body. Meanwhile, pH 6.8 phosphate buffer medium was also used in the study, as it was more typically used in formulation development/screening process, pH 6.8 phosphate buffer medium is not as indicated as FaSSIF medium in terms of establishing the IVIVC.

If the API recrystallizes during the dissolution, its solubility will drop and its concentration in the dissolution media will decrease. This will show up as a lower trend after reaching a local maximum. The objective is, with the help of HPMC-MP polymer the API can maintain at a high level without ever going lower. This property is described as anti-nucleation capability.

There are multiple parameters derived from the dissolution profile. AUC is the area under curve for dissolution profiles, and it is an indicator of how much API can be absorbed by body. Cmax is the highest concentration of the dissolution. Tmax is the time point corresponding to Cmax. relAUC is the ratio of the AUC of the polymer enhanced solubility v.s. the AUC of the neat API itself. The higher value suggests the better solubility enhancement capability. C120/Cmax is the concentration at the last time point divided by its highest concentration, with the highest value of 1. The higher value suggests the better anti-nucleation capability.

Dissolution Results Summary: Efavirenz SDD in FaSSIF Media

| Sample | AUC (min μg/mL) | C120 (μg/mL) | Cmax (μg/mL) | Tmax (min) | relAUC | C120/Cmax |
|---|---|---|---|---|---|---|
| Efavirenz | 18702.91 | 166.7892 | 166.7892 | 120 | 1.0 | 1 |
| 148 | 30472.58 | 306.8982 | 306.8982 | 120 | 1.6 | 1 |
| 149 | 27491.28 | 261.6166 | 261.6166 | 120 | 1.5 | 1 |
| 151 | 31731.6 | 300.2469 | 300.2469 | 120 | 1.7 | 1 |
| 161 | 28221.13 | 271.3078 | 271.3078 | 120 | 1.5 | 1 |
| 165 | 37548.25 | 375.871 | 375.871 | 120 | 2.0 | 1 |

Dissolution Results Summary: Efavirenz SDD in pH 6.8 Phosphate Buffer Media

| Sample | AUC (min μg/mL) | C120 (μg/mL) | Cmax (μg/mL) | Tmax (min) | relAUC | C120/Cmax |
|---|---|---|---|---|---|---|
| Efavirenz | 960.92 | 9.92448 | 10.36102 | 100 | 1.0 | 0.96 |
| 148 | 2345.32 | 31.16284 | 31.16284 | 120 | 2.4 | 1.00 |
| 149 | 3844.462 | 31.60316 | 75.20709 | 5.5 | 4.0 | 0.42 |
| 151 | 22968.01 | 199.0975 | 260.6348 | 4.5 | 23.9 | 0.76 |
| 161 | 3056.078 | 43.02913 | 43.02913 | 120 | 3.2 | 1.00 |
| 165 | 3116.844 | 46.49899 | 46.49899 | 120 | 3.2 | 1.00 |

Differential Scanning Calorimetry (DSC): Glass transition temperature Tg is an important indicator of API physical stability against crystallization through storage. The higher Tg, the better physical stability. Generally speaking, if the Tg is equal to or higher than storage temperature+50° C., then the product is expected to be very stable throughout the entire shelf life. If the Tg is between storage temperature and temperature+50° C., then some stability issue may occur.

The glass transition temperature (Tg) measurement were conducted using TA instrument, Q2000. For pure ingredients, regular DSC set up was used. A heat-cool-heat cycle with a heating rate of 10° C./minutes was implemented. The first heating cycle is used to standardize sample by erasing its thermal history, and the Tg from second heating cycle is reported. For SDD, modulated DSC set up was used. An average heating rate of 2° C./minute with modulation amplitude of 1° per 40 seconds was implemented.

The measurement results are summarized below in the Table. The Table shows that all SDDs have Tg values about 30-40° C. higher than room temperature. Stable SDDs are expected from this indicator. Meanwhile, all SDDs exhibit single Tg, suggesting that there is no phase separation for either SDD.

Glass Transition Temperature (Tg) Summary

| Sample | Tg (° C.), Pure ingredient | Tg (° C.), Spray Dried Dispersion |
|---|---|---|
| Efavirenz | 34.9 | N/A |
| 148 | 106.2 | 58.7 |
| 149 | 97.9 | 57.9 |
| 151 | 95.3 | 57.7 |
| 161 | 95.8 | 55.6 |
| 165 | 114.7 | 64.1 |

Example 7

Synthesis of Ethylpyrrolidone Glycidylether-Carboxymethyl Cellulose (EPGE-CMC) Starting from Cellulose in Isopropyl Alcohol Solvent System For a typical preparation, 67.71 g of cellulose was charged into the reactor. A solvent mixture of 657.85 g isopropyl alcohol (IPA) and 73.41 g water was then added. 50% NaOH solution (81 g) was dosed. The slurry was kept at room temperature for 1 h, followed by addition of 88.3 g MCA in IPA solution (50%). The reactor was heated to 70° C. and kept at this temperature for 75 minutes. Then 74.2 g EPGE was added. After holding the reactor at 70° C. for 180 minutes, it was cooled to room temperature. Acetic acid was used to adjust pH. The slurry was washed with methanol/water mixture three times, followed by a pure methanol final wash. The product was dried on a fluid bed dryer and ground using a 0.5 mm screen.

Example 8

Synthesis of Ethylpyrrolidone Glycidylether-Carboxymethyl Cellulose (EPGE-CMC) Starting from Cellulose in Heptane Solvent System For a typical preparation, 45.37 g of cellulose was charged into the reactor. A solvent mixture of 440.77 g heptane and 49.19 g water was then added. 50% NaOH solution (53.04 g) was dosed. The slurry was kept at room temperature for 1 h, followed by addition of 59.16 g MCA in IPA solution (50%). The reactor was heated to 70° C. and kept at this temperature for 75 minutes. The reactor was cooled down to room temperature. On the second day, the reactor was heated to 75° C. Then 99.4 g EPGE was added. After holding the reactor at 75° C. for 360 minutes, it was cooled to room temperature. Acetic acid was used to adjust pH. The slurry was washed with acetone/water mixture several times, followed by a pure acetone final wash. The product was dried on a fluid bed dryer and ground using a 0.5 mm screen.

The CMC-EPGE hybrids were tested as binder for Si-based anodes in LiB application. Preliminary results showed expected benefits on slurry processing and uniform coated electrode. Higher EPGE MS hybrid has better electrochemistry in cycling and rate performance.

The following compound was prepared according to the method set out in Example 7 and 8.

Synthesis of EPGE-CMC Under Different Conditions

Synthesis of EPGE-CMC under different conditions

| Sample | Target | Cellulose type | EPGE/ AGU equiv | Solvent | Viscosity, cPs | Solution Concentration |
|---|---|---|---|---|---|---|
| 19 | CMC-mark | Southern 1059 | NA | IPA | 7600 | 1% |
| 21 | CMC-EPGE | Southern 1059 | 0.5 | IPA | 8220 | 1% |
| 23 | CMC-EPGE | Southern 1059 | 1 | IPA | 6780 | 1% |
| 45 | CMC-EPGE | Southern 1059 | 2 | Heptane | 300 | 1% |
| 47 | CMC-EPGE | Southern 1059 | 1 | Heptane | 13 | 1% |
| 51 | CMC-EPGE | GP3865 | 1.0 | Heptane | 2840 | 5% |
| 55 | CMC-EPGE | GP3865 | 0.5 | Heptane | 3400 | 5% |
| 75 | CMC-EPGE | GP3822 | 1.0 | Heptane | 180 | 1% |
| 77 | CMC-EPGE | GP3822 | 0.5 | Heptane | 60 | 1% |

Example 9

Synthesis of EPGE-HEC Starting from Cellulose

For a typical preparation, 70 g of cellulose was charged into the Labmax reactor. A solvent mixture of 464 g IPA, TBA, water and acetone was then added. NaOH 50% solution (43 grams) was dosed, followed by 69.55 g of ethylene oxide. The reactor was heated to 45° C. and kept at this temperature for 45 minutes, then the reactor was further heated to 90° C. and held for 60 minutes. The reactor was cooled down to 60° C., and 39 g of EPGE was added. After holding the reactor at 60° C. for 180 minutes, it was cooled to room temperature, and 47 g of nitric acid and 0.8 g of acetic acid was added. The slurry was washed with an acetone/water mixture four times, followed by a pure acetone final wash. The product was dried on a fluid bed dryer and ground using a 0.5 mm screen.

Example 10

Synthesis of EPGE-HMHEC Starting from Cellulose

The labmax production starts from unmodified cellulose. New Bern 421 and Flint River 421 were used as starting cellulose and C16 was applied as hydrophobe. Once HMHEC was made, the temperature dropped to 60° C. and EPGE was added. Then the reaction was kept at 60° C. for 3 hs, followed by the cooling to room temp. Finally, nitric acid was added to neutralize the slurry mixture. The crude product was washed with acetone/water mixture for several times.

Preliminary durable stiffness of hair tresses test showed low EPGE substitution seems good, but need to do more test to find an optimum substitution. Coatings test of hybrids showed similar thickening efficiency vs. unmodified HEC.

The following compounds were prepared according to the method set out in Example 9.

| Sample | Target | Cellulosics | EPGE/AGU equiv | Mw | Viscosity, cPs | Solution Concentration |
|---|---|---|---|---|---|---|
| 106 | 250L HEC benchmark | GP3865 | NA | 448000 | 2440 | 5% |
| 118 | 250L HEC-EPGE | GP3865 | 0.5 | 486000 | 3380 | 5% |
| 53 | 250L HEC-EPGE | GP3865 | 1 | 456000 | 2980 | 5% |
| 149 | 250H HEC benchmark | Buckeye UVE Cellulose | NA | 1520000 | 2080 | 1% |
| 164 | 250H HEC-EPGE | Buckeye UVE Cellulose | 0.25 | 1550000 | 1880 | 1% |
| 83 | 250H HEC-EPGE | Buckeye UVE Cellulose | 0.5 | 1260000 | 900 | 1% |
| 188 | 250H HEC benchmark | Buckeye UVE Cellulose | NA | 1250000 | 3420 | 1% |
| 3 | 250H HEC-EPGE | Buckeye UVE Cellulose | 0.1 | 1510000 | 2960 | 1% |
| 191 | 250H HEC-EPGE | Buckeye UVE Cellulose | 0.25 | 1230000 | 3400 | 1% |
| 194 | 250H HEC-EPGE | Buckeye UVE Cellulose | 0.5 | 1310000 | 2660 | 1% |
| 197 | 250H HEC-EPGE | Buckeye UVE Cellulose | 0.75 | | 2920 | 1% |

The following compounds were prepared according to the method set out in Example 10.

| Sample | Target | Cellulosics | EPGE/AGU equiv | Mw | Viscosity, cPs | Solution Concentration |
|---|---|---|---|---|---|---|
| 131 | HMHEC control | NB421 + FR421 | NA | 663000 | 1340 | 1% |
| 71 | HMHEC-EPGE | NB421 + FR421 | 0.5 | 809000 | 760 | 1% |
| 73 | HMHEC-EPGE | NB421 + FR421 | 1 | 834000 | 250 | 1% |
| 104 | HMHEC control | NB421 + FR421 | NA | 563000 | 1200 | 2.5% |
| 110 | HMHEC-EPGE | NB421 + FR421 | 0.5 | 678000 | 1980 | 2.5% |
| 143 | HMHEC-EPGE | NB421 + FR421 | 0.75 | 561000 | 1620 | 2.5% |

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:

1. A hybrid polymer having the structure:

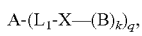

wherein A is a cellulose ether moiety comprising a —OH group;

$L_1$ is a linking group moiety selected from the group consisting of urethanes, carbonates, and phosphate esters;

X is a spacer group moiety, selected from the group consisting of straight- or branched-chain functionalized and unfunctionalized alkyl, cycloalkyl, alkenyl, and aryl groups, wherein any of the above groups is without heteroatoms, or is a direct bond; and B is a lactam moiety;

wherein k≥1 and q≥1.

2. The hybrid polymer according to claim 1, wherein A has the following structure:

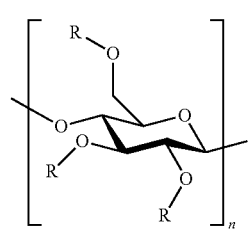

wherein R is independently selected from the group consisting of (i) hydrogen; (ii) $C_1$ to $C_{50}$ straight- or branched-chain functionalized or unfunctionalized alkyl, cycloalkyl, aryl, cycloaryl, alkoxy, aryloxy, cycloalkoxy, cycloaryloxy groups; (iii) hydroxyalkyl functional groups; (iv) alkylcarboxy groups; and (v) functionalized and non-functionalized, substituted or free carbonyl groups; wherein the above functional groups is without heteroatoms; and n is from 1 to about 2000; wherein at least one R is covalently bonded to a lactam group moiety, via a linking group moiety and spacer group moiety, respectively.

3. The hybrid polymer according to claim 2, wherein the cellulose ether moiety A is selected from the group consisting of methylcellulose, ethylcellulose, methyl(hydroxyethyl) cellulose, hydroxyethyl cellulose, hydrophobically modified hydroxyethyl cellulose, carboxymethyl hydroxyethyl cellulose, carboxymethyl cellulose, hydroxypropyl methyl cellulose, ethyl(hydroxyethyl) cellulose, and hydroxypropylcellulose.

4. The hybrid polymer according to claim 3, wherein the cellulose ether moiety A is selected from the group consisting of methylcellulose, carboxymethyl cellulose, hydroxyethyl cellulose, and hydroxypropyl methylcellulose.

5. The hybrid polymer according to claim 1, wherein the X spacer group moiety is selected from the group consisting of $C_1$ to $C_{50}$ straight- or branched-chain functionalized and unfunctionalized alkyl, cycloalkyl, alkenyl, and aryl groups, wherein any of the above groups may be with or without heteroatoms.

6. The hybrid polymer according to claim 1, wherein the lactam moiety B has the following structure:

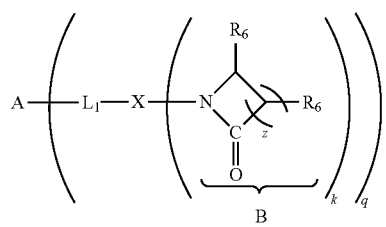

wherein $R_6$ is selected from the group consisting of hydrogen, functionalized and unfunctionalized alkyl, cycloalkyl, alkenyl, and aryl groups; and mixtures thereof; wherein z=0 to 4.

7. The hybrid polymer according to claim 6, wherein the lactam moiety B is selected from the group consisting of α-lactam (α-aziridinone), β-lactam (β-propiolactam), γ-lactam (γ-butyrolactam), δ-lactam (δ-valerolactam), and ε-lactam (ε-caprolactam).

8. The hybrid polymer according to claim 1, wherein the hybrid polymer is the product derived from the chemical reaction of A, wherein A is derived from a cellulose ether moiety comprising a —OH group, wherein the structure of A is set out below:

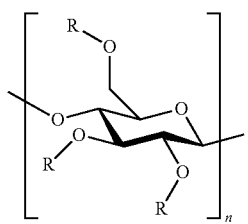

A wherein R is independently selected from the group consisting of (i) hydrogen; (ii) $C_1$ to $C_{50}$ straight- or branched-chain functionalized or unfunctionalized alkyl, cycloalkyl, aryl, cycloaryl, alkoxy, aryloxy, cycloalkoxy, cycloaryloxy groups; (iii) hydroxyalkyl functional groups; (iv) alkylcarboxy groups; and (v) functionalized and non-functionalized, substituted or free carbonyl groups; wherein the above functional groups may be with or without heteroatoms; and n is from 1 to about 2000;

wherein at least one R is covalently bonded to a lactam group moiety, via a linking group Moiety and spacer group moiety, respectively;

and Q, wherein the structure of Q is set out below:

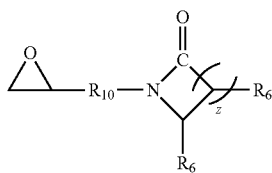

Q wherein $R_6$ is selected from the group consisting of hydrogen, functionalized and unfunctionalized alkyl, cycloalkyl, alkenyl, and aryl groups; and mixtures thereof; wherein z 0 to 4; $R_{10}$ is selected from the group consisting of straight- or branched-chain functionalized and unfunctionalized alkyl, cycloalkyl, alkenyl, and aryl groups, wherein any of the above groups may be with or without heteroatoms, or is a direct bond; wherein z=0 to 4.

9. A hybrid polymer having the structure:

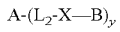

wherein A is a cellulose ether moiety comprising a —OH group;

$L_2$ is an ether linking group moiety;

X is a spacer group moiety, selected from the group consisting of straight- or branched-chain functionalized and unfunctionalized alkyl, cycloalkyl, alkenyl, and aryl groups, wherein any of the above groups is without heteroatoms, or is a direct bond; and B is a lactam moiety;

wherein y≥1;

with the proviso that when the cellulose ether moiety is hydroxyethyl cellulose, -($L_2$-X—B$)_y$ is not obtained from 1-(hydroxymethyl)-2-pyrrolidinone.

10. The hybrid polymer according to claim 9, wherein A has the following structure:

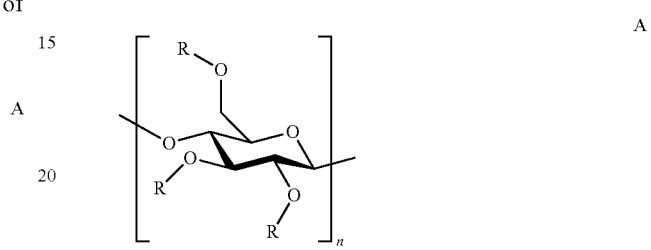

A wherein R is independently selected from the group consisting of (i) hydrogen; (ii) $C_1$ to $C_{50}$ straight- or branched-chain functionalized or unfunctionalized alkyl, cycloalkyl, aryl, cycloaryl, alkoxy, aryloxy, cycloalkoxy, cycloaryloxy groups; (iii) hydroxyalkyl functional groups; (iv) alkylcarboxy groups; and (v) functionalized and non-functionalized, substituted or free carbonyl groups; wherein the above functional groups may be with or without heteroatoms; and n is from 1 to about 2000; wherein at least one R is covalently bonded to a lactam group moiety, via a linking group moiety and spacer group moiety, respectively.

11. The hybrid polymer according to claim 10, wherein the cellulose ether moiety A is selected from the group consisting of methylcellulose, ethylcellulose, methyl(hydroxyethyl) cellulose, hydroxyethyl cellulose, hydrophobically modified hydroxyethyl cellulose, carboxymethyl hydroxyethyl cellulose, carboxymethyl cellulose, hydroxypropyl methyl cellulose, ethyl(hydroxyethyl) cellulose, and hydroxypropylcellulose.

12. The hybrid polymer according to claim 11, wherein the cellulose ether moiety A is selected from the group consisting of methylcellulose, carboxymethyl cellulose, hydroxyethyl cellulose, and hydroxypropyl methylcellulose.

13. The hybrid polymer according to claim 9, wherein the X spacer group moiety is selected from the group consisting of $C_1$ to $C_{50}$ straight- or branched-chain functionalized and unfunctionalized alkyl, cycloalkyl, alkenyl, and aryl groups, wherein any of the above groups is without heteroatoms.

14. The hybrid polymer according to claim 9, wherein the lactam moiety B has the following structure:

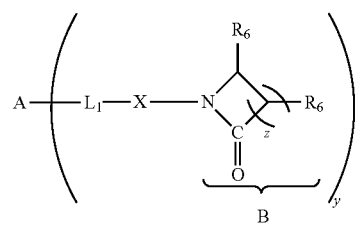

B wherein $R_6$ is selected from the group consisting of hydrogen, functionalized and unfunctionalized alkyl, cycloalkyl, alkenyl, and aryl groups; and mixtures thereof; wherein z 0 to 4.

15. The hybrid polymer according to claim 14, wherein the lactam moiety B is selected from the group consisting of α-lactam (α-aziridinone), β-lactam (β-propiolactam), γ-lactam (γ-butyrolactam), δ-lactam (δ-valerolactam), and ε-lactam (ε-caprolactam).

16. A composition comprising a hybrid polymer having the structure:

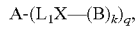

wherein A is a cellulose ether moiety comprising a —OH group;

$L_1$ is a linking group moiety selected from the group consisting of urethanes, carbonates, and phosphate esters;

X is a spacer group moiety, selected from the group consisting of straight- or branched-chain functionalized and unfunctionalized alkyl, cycloalkyl, alkenyl, and aryl groups, wherein any of the above groups is without heteroatoms, or is a direct bond; and B is a lactam moiety;

wherein k≥1 and q≥1.

17. A composition comprising a hybrid polymer having the structure:

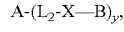

wherein A is a cellulose ether moiety comprising a —OH group;

$L_2$ is an ether linking group moiety;

X is a spacer group moiety, selected from the group consisting of straight- or branched-chain functionalized and unfunctionalized alkyl, cycloalkyl, alkenyl, and aryl groups, wherein any of the above groups is without heteroatoms, or is a direct bond; and B is a lactam moiety;

wherein y≥1;

with the proviso that when the cellulose ether moiety is hydroxyethyl cellulose, $-(L_2-X-B)_y$, is not obtained from 1-(hydroxymethyl)-2-pyrrolidinone.

* * * * *